United States Patent [19]

Malamas et al.

[11] Patent Number: 4,743,611

[45] Date of Patent: May 10, 1988

[54] NAPHTHALENYLSULFONYLIMIDAZOLIDINEDIONES AND THEIR THIOXO ANALOGS USEFUL AS ALDOSE REDUCTASE INHIBITORS

[75] Inventors: Michael S. Malamas, Plainsboro; Kazimir Sestanj, Monmouth Junction, both of N.J.

[73] Assignee: American Home Products Corp., New York, N.Y.

[21] Appl. No.: 12,592

[22] Filed: Feb. 9, 1987

Related U.S. Application Data

[63] Continuation-in-part of Ser. No. 881,377, Jul. 2, 1986, abandoned.

[51] Int. Cl.[4] .................. A61K 31/415; C07D 403/30
[52] U.S. Cl. ...................................... 514/390; 548/311
[58] Field of Search ......................... 548/311; 514/390

[56] References Cited

PUBLICATIONS

I. Miwa, Biochemical Pharmacology, 36, 2789–2794 (1987).
J. Okuda et al., Seventh International Congress of Eye Research, held in Nagoya, Japan, Sep. 25 to Oct. 1, 1986, p. 175. Abstract.

*Primary Examiner*—John M. Ford
*Assistant Examiner*—Robert C. Whittenbaugh
*Attorney, Agent, or Firm*—Walter Patton

[57] ABSTRACT

Disclosed herein are naphthalenylsulfonylimidazolidinediones and their thioxo analogs and methods for their preparation. The compounds are new aldose reductase inhibitors useful for the treatment or prevention of diabetic complications.

25 Claims, No Drawings

NAPHTHALENYLSULFONYLIMIDAZOLIDINEDIONES AND THEIR THIOXO ANALOGS USEFUL AS ALDOSE REDUCTASE INHIBITORS

This is a continuation-in-part application of copending U.S. patent application U.S. Ser. No. 881,377, filed July 2, 1986, now abandoned.

BACKGROUND OF THE INVENTION

This invention relates to substituted naphthalenylsulfonylimidazolidinediones and their thioxo analogs, to processes for their preparation, to methods for using the compounds, and to pharmaceutical preparations thereof. The compounds have pharmaceutical properties which render them beneficial for the treatment of diabetes mellitus and associated conditions.

For many years diabetes mellitus has been treated with two established types of drugs, namely insulin and oral hypoglycemic agents. These drugs have benefited hundreds of thousands of diabetics by improving their well-being and prolonging their lives. However, the resulting longevity of diabetic patients has led to complications such as neuropathy, nephropathy, retinopathy, cataracts and atherosclerosis. These complications have been linked to the undesirable accumulation of sorbitol in diabetic tissue, which in turn resulted from the high levels of glucose characteristic of the diabetic patient.

In mammals, including humans, the key enzyme involved in the conversion of hexoses to polyols (e.g. the sorbitol pathway) is aldose reductase. J. H. Kinoshita and collaborators [see J. H. Kinoshita et al, Biochem. Biophys. Acta, 158, 472 (1968) and references cited therein] have demonstrated that aldose reductase plays a central role in the etiology of galactosemic cataracts by effecting the conversion of galactose to dulcitol (galactitol) and that an agent capable of inhibiting aldose reductase can prevent the detrimental accumulation of dulcitol in the lens. Furthermore, a relationship between elevated levels of glucose and an undesirable accumulation of sorbitol has been demonstrated in the lens, peripheral nervous cord and kidney of diabetic animals, see A. Pirie and R. van Heyningen, Exp. Eye Res., 3, 124 (1964); L. T. Chylack and J. H. Kinoshita, Invest. Ophthal., 8, 401 (1969) and J. D. Ward and R. W. R. Baker, Diabetol., 6, 531 (1970).

The relevant prior art is as follows.

K. Sestanj, et al, U.S. Pat. No. 4,568,693, Feb. 4, 1986, disclose N-naphthoylglycine derivatives effective as aldose reductase inhibitors. J. Okuda et al, Japanese Patent No. 58/109-418-A (1981); K. Inagaki et al, Chem. Pharm. Bull., 30(9), 3244–3254 (1982); I. Miwa, et al, Chem. Pharm. Bull., 32(5), 2030–2032 (1984); and J. Okuda, et al, Chem. Pharm. Bull., 33(7), 2990–2995 (1985) disclose 1-(phenylsulphonyl)hydantoins useful as aldose reductase inhibitors. V. G. Zubenko, et al, Farmatsevt Zh. (Kiev) 16(2), 10–15 (1961) disclose derivatives of azolidine useful as antidiabetic compounds. I. S. Bengelsdorf, J. Am. Chem. Soc., 75, 3138–3140 (1953) discloses preparation of benzenesulfonylhydantoins.

Japanese patent application publication number Ja.15187/68 discloses sulfonyl hydantoin derivatives substituted on the carbon atom of the hydantoin ring. These compounds have anti-convulsant activity.

The present application discloses novel substituted naphthalenylsulfonylimidazolidinediones and their thioxo analogs represented below by formula (I), which are more effective inhibitors of aldose reductase than the reported benzenesulfonylhydantoins. They are useful for the treatment of conditions associated with diabetes mellitus such as neuropathy, retinopathy, nephropathy, cataracts and atherosclerosis. The compounds of formula (I) below increase visual acuity. These compounds show hypoglycemic activity and are useful in the treatment of some forms of diabetes. They also stabilize the weight of the subject by inhibiting weight gain. These compounds are also useful for the treatment of cardiac autonomic dysfunction and for lowering blood pressure.

These compounds are free of central nervous system side effects such as anti-convulsant activity.

SUMMARY OF THE INVENTION

The naphthalenylsulfonylimidazolidinediones and their thioxo analogs of this invention are represented by formula (I)

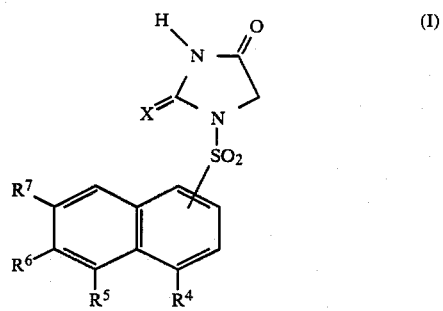

wherein $R^4$, $R^5$, $R^6$ and $R^7$ are independently hydrogen, halogen, trifluoromethyl, methoxy or dimethylamino group and X is oxygen or sulfur and the pharmaceutically acceptable salts thereof. Formula (I) is intended to represent bonding of the sulfonyl group at either the 1- or the 2-position of the naphthalene ring.

A preferred group of compounds of the present invention is represented by the formula (II) wherein the sulfonyl group is bonded at the 1-position of the naphthalene ring

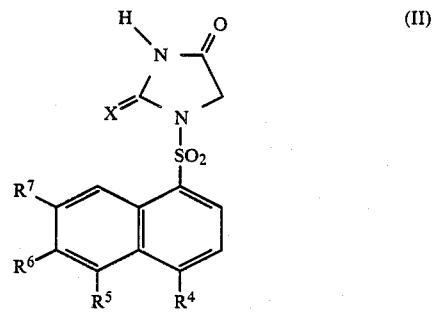

wherein $R^4$, $R^5$, $R^6$ and $R^7$ are hydrogen, halogen, trifluoromethyl, methoxy or dimethylamino group and X is oxygen or sulfur and the pharmaceutically acceptable salts thereof.

A further preferred group of compounds of the present invention is represented by the formula (II) wherein $R^4$, $R^5$, $R^6$ and $R^7$ are hydrogen or halogen and X is sulfur or oxygen.

A still further preferred group of compounds of the present invention is represented by the formula (II)

wherein $R^4$, $R^6$ and $R^7$ are hydrogen, $R^5$ is halogen and X is oxygen. The active halogen compounds are bromine, chlorine and iodine in decreasing order of activity.

The most preferred compounds of the present invention are set forth below:

1-[(5-bromo-1-naphthalenyl)sulfonyl]-2,4-imidazolidinedione;
1-[(5-bromo-1-naphthalenyl)sulfonyl]-2-thioxo-4-imidazolidinone;
1-[(4-bromo-1-naphthalenyl)sulfonyl]-2,4-imidazolidinedione;
1-[(4-bromo-1-naphthalenyl)sulfonyl]-2-thioxo-4-imidazolidinone;
1-[[6-methoxy-5-(trifluoromethyl)-1-naphthalenyl]sulfonyl]-2,4-imidazolidinedione;
1-[[6-methoxy-5-(trifluoromethyl)-1-naphthalenyl]sulfonyl]-2-thioxo-4-imidazolidinone;
1-[[5-(dimethylamino)-1-naphthalenyl]sulfonyl]-2,4-imidazolidinedione and the pharmaceutically acceptable salt thereof;
1-[[5-(dimethylamino)-1-naphthalenyl]sulfonyl]-2-thioxo-4-imidazolidinone and the pharmaceutically acceptable salt thereof;
1-[(1-naphthalenyl)sulfonyl]-2-thioxo-4-imidazolidinone;
1-[(1-naphthalenyl)sulfonyl]-2,4-imidazolidinedione;
1-[(6-bromo-1-naphthalenyl)sulfonyl]-2-thioxo-4-imidazolidinone;
1-[(6-bromo-1-naphthalenyl)sulfonyl]-2,4-imidazolidinedione;
1-[(7-bromo-1-naphthalenyl)sulfonyl]-2-thioxo-4-imidazolidinone;
1-[(7-bromo-1-naphthalenyl)sulfonyl]-2,4-imidazolidinedione;
1-[(5-iodo-1-naphthalenyl)sulfonyl]-2-thioxo-4-imidazolidinone;
1-[(5-iodo-1-naphthalenyl)sulfonyl]-2,4-imidazolidinedione;
1-[(5-chloro-1-naphthalenyl)sulfonyl]-2,4-imidazolidinedione; and
1-[(5-chloro-1-naphthalenyl)sulfonyl]-2-thioxo-4-imidazolidinone.

The compounds of the present invention wherein the sulfonyl group is bonded at the 2-position of the naphthalene ring are represented by formula (III)

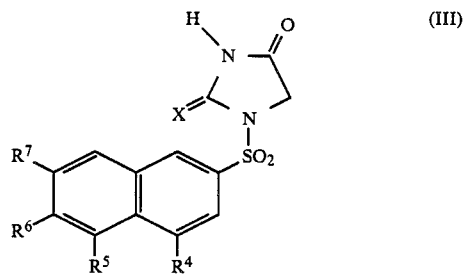

wherein $R^4$, $R^5$, $R^6$ and $R^7$ are hydrogen, halogen, trifluoromethyl, methoxy or dimethylamino group and X is oxygen of sulfur.

A preferred group of compounds of the present invention is represented by formula (III) wherein $R^4$, $R^6$ and $R^7$ are hydrogen, $R^5$ is halogen and X is sulfur or oxygen.

A further preferred group of compounds is set forth below:

1-[(5-bromo-2-naphthalenyl)sulfonyl]-2,4-imidazolidinedione; and
1-[(5-bromo-2-naphthalenyl)sulfonyl]-2-thioxo-4-imidazolidinone.

The naphthalenylsulfonylimidazolinediones and their thioxo analogs were prepared by the processes described hereinafter.

A method is provided for preventing or relieving diabetes mellitus associated complications in a diabetic mammal by administering to said mammal a prophylactic or alleviating amount of the compound of formula (I). Such complications include neuropathy, nephropathy, retinopathy and cataracts.

The compound of formula (I), when admixed with a pharmaceutically acceptable carrier, forms a pharmaceutical composition which can be used according to the preceding method.

DETAILED DESCRIPTION OF THE INVENTION

The naphthalenylsulfonylimidazolidinediones and their thioxo analogs of this invention may be administered to mammals, for example, man, cattle or rabbits, either alone or in dosage forms, i.e., capsules or tablets, combined with pharmacologically acceptable excipients.

The compounds of this invention may be given orally. However, the method of administering the present active ingredients of this invention is not to be construed as limited to a particular mode of administration. For example, the compounds may be administered topically directly to the eye in the form of drops of sterile, buffered ophthalmic solutions, preferably of pH 7.2-7.6. Also, they may be administered orally in solid form containing such excipients as starch, milk sugar, certain types of clay and so forth. They may also be administered orally in the form of solutions or they may be injected parenterally. For parenteral administration they may be used in the form of a sterile solution, preferably of pH 7.2-7.6, containing a pharmaceutically acceptable buffer.

The dosage of the naphthalenylsulfonylimidazolidinediones and their thioxo analogs will vary with the form of administration and the particular compound chosen. Furthermore, it will vary with the particular host under treatment. Generally, treatment is initiated with small dosages substantially less than the optimal dose of the compound. Therefore, the dosage is increased by small increments until efficacy is obtained. In general, the compounds of this invention are most desirably administered at a concentration level that will generally afford effective results without causing any harmful or deleterious side effects. For topical administration, a 0.05-0.2% solution may be administered dropwise in the eye. The frequency of instillation varies with the subject under treatment from a drop every two or three days to once daily. For oral or parenteral administration a preferred level of dosage ranges from about 0.1 mg to about 200 mg per kilo of body weight per day, although aforementioned variations will occur. However, a dosage level that is in the range of from about 3.0 mg to about 30 mg per kilo of body weight per day is most satisfactory.

Unit dosage forms such as capsules, tablets, pills and the like may contain from about 5.0 mg to about 250 mg of the active ingredients of this invention with a pharmaceutical carrier. Thus, for oral administration, capsules can contain from between about 5.0 mg to about 250 mg of the active ingredients of this invention with or without a pharmaceutical diluent. Tablets, either effervescent or noneffervescent, can contain between about 5.0 to 250 mg of the active ingredients of this invention together with conventional pharmaceutical carriers. Thus, tablets, which may be coated and either effervescent or noneffervescent, may be prepared according to the known art. Inert diluents or carriers, for example, magnesium carbonate or lactose, can be used together with conventional disintegrating agents for example, magnesium stearate.

The naphthalenylsulfonylimidazolidinediones and their thioxo analogs also can be used in combination with insulin or oral hypoglycemic agents to produce a beneficial effect in the treatment of diabetes mellitus. In this instance, commercially available insulin preparations or oral hypoglycemic agents, exemplified by acetohexamide, chlorpropamide, tolazamide, tolbutamide and phenformin, are suitable. The compounds hereof can be administered sequentially or simultaneously with insulin or the oral hypoglycemic agent. Suitable methods of administration, compositions and doses of the insulin preparation or oral hypoglycemic agent are described in medical textbooks; for instance, "Physicians' Desk Reference", 36 ed., Medical Economics Co., Oradell, N.J., U.S.A., 1982.

The aldose reductase inhibiting property of the compounds of this invention and the utilization of the compounds in preventing, diminishing and alleviating diabetic complications are demonstrable in experiments using galactosemic rats, see Dvornik et al., cited above. Such experiments are exemplified hereinbelow after the listing of the following general comments pertaining to these experiments:

(a) Four or more groups of six male rats, 50–70 g, Sprague-Dawley strain, were used. The first group, the control group, was fed a mixture of laboratory chow (rodent Laboratory Chow, Purina) and glucose at 20% (w/w %) concentration. The untreated galactosemic group was fed a similar diet in which galactose is substituted for glucose. The third group was fed a diet prepared by mixing a given amount of the test compound with the galactose containing diet. The concentration of galactose in the diet of the treated groups was the same as that for the untreated galactosemic group.

(b) After four days, the animals were killed by decapitation. The eyeballs were removed and punctured with a razor blade; the freed lenses were rolled gently on filter paper and weighed. The sciatic nerves were dissected as completely as possible and weighed. Both tissues when frozen can be kept up to two weeks before being analyzed for dulcitol.

(c) The polyol determination was performed by a modification of the procedure of M. Kraml and L. Cosyns, Clin. Biochem., 2,373 (1969). Only two minor reagent changes were made: (a) The rinsing mixture was an aqueous 5% (w/v) trichloroacetic acid solution and (b) the stock solution was prepared by dissolving 25 mg of dulcitol in 100 ml of an aqueous trichloroacetic acid solution. [N.B.: For each experiment the average value found in the tissue from rats fed the glucose diet was subtracted from the individual values found in the corresponding tissue in galactose-fed rats to obtain the amount of polyol accumulated.] The aldose reductase inhibiting effects of the compounds of formula (I) were also tested by employing an in vitro testing procedure similar to that described by S. Hayman and J. H. Kinoshita, J. Biol. Chem., 240, 877 (1965).

In the present case the procedure of Hayman and Kinoshita was modified in that the final chromatography step was omitted in the preparation of the enzyme from bovine lens.

The following tabulated results show that the naphthalenylsulfonylimidazolidinediones and their thioxo analogs of this invention show the property that they are active both in vitro and in vivo and diminish the accumulation of dulcitol in the lenses, sciatic nerves and diaphragm of rats fed galactose. The figures under L, N and D represent the percentage decrease of dulcitol accumulation in the tissues of the lens, sciatic nerve and diaphragm, respectively, for treated rats as compared to untreated rats.

Examination of the results tabulated below show that the naphthalenylsulfonylimidazolidinediones and their thioxo analogs of this invention are quite potent as aldose reductase inhibitors. For example, the compound of Example No. 2 1-[(5-bromo-1-naphthalenyl)sulfonyl]-2,4-imidazolidinedione in Table 1, at a dose of 4.8 and 10.2 mg/kg/day gives comparable results to the last compound in Table 1, N-[[6-methoxy-5-(trifluoromethyl)-1-naphthalenyl]thioxomethyl]-N-methylglycine at a dose of 4 and 11 mg/kg/day.

TABLE 1

Inhibition of Aldose Reductase by Compounds of Formula (II)

| Example No. | $R^4$ | $R^5$ | $R^6$ | $R^7$ | X | % inhibition in vitro $10^{-5}$ | $10^{-6}$ | $10^{-7}$ | mg/kg/day | L | N | D | m.p. °C. | Process |
|---|---|---|---|---|---|---|---|---|---|---|---|---|---|---|
| 1 | H | Br | H | H | S | 67 | 17 | — | 109 | 49 | 90 | 86 | 235–237 | A |

TABLE 1-continued

| | | | | | | % inhibition in vitro | | | % lowering dulcitol accumulation in vivo | | | | | Pro- |
| | | | | | | | | | mg/ | | | | | |
| | | | | | | $10^{-5}$ | $10^{-6}$ | $10^{-7}$ | kg/day | L | N | D | m.p. °C. | cess |
|---|---|---|---|---|---|---|---|---|---|---|---|---|---|---|
| | | | | | | | | | 48 | 40 | 68 | 64 | | |
| | | | | | | | | | | ($p < 0.01$) | ($p < 0.01$) | ($p < 0.01$) | | |
| | | | | | | | | | 24 | 24 | 56 | 61 | | |
| | | | | | | | | | | ($p < 0.01$) | ($p < 0.01$) | ($p < 0.01$) | | |
| | | | | | | | | | 9.4 | 13 | NS | 36 | | |
| | | | | | | | | | | ($p < 0.1$) | — | ($p < 0.01$) | | |
| | | | | | | | | | 5.1 | NS | NS | NS | | |
| | | | | | | | | | $ED_{50}$ | 99 | 22 | 18 | | |
| 2 | H | Br | H | H | O | 93 | 89 | 45 | 101 | 79 | 67 | 87 | 227–228 | A |
| | | | | | | | | | 23 | 44 | 43 | 81 | | |
| | | | | | | | | | 20.7 | 36 | 60 | 75 | | |
| | | | | | | | | | 10.2 | 18 | 57 | 72 | | |
| | | | | | | | | | 4.8 | NS | 42 | 58 | | |
| | | | | | | | | | $ED_{50}$ | — | 8.1 | 2.0 | | |
| 3 | Br | H | H | H | S | 53 | 15 | — | 24 | NS | NS | NS | 239 (dec.) | A |
| 4 | Br | H | H | H | O | 92 | 81 | 31 | 24 | NS | 59 | 27 | 234–236 | A |
| | | | | | | | | | | | ($p < 0.1$) | | | |
| 5 | H | $CF_3$ | $OCH_3$ | H | S | 40 | 15 | — | 23 | NS | NS | NS | 260 (dec.) | A |
| 6 | H | $CF_3$ | $OCH_3$ | H | O | 86 | 84 | 43 | 86 | 60 | N.D. | 87 | 273–274 | B |
| | | | | | | | | | | ($p < 0.01$) | — | ($p < 0.01$) | | |
| 7 | H | $NMe_2$ | H | H | S | 58 | 12 | — | 96 | NS | N.D. | NS | 220 (dec.) | A |
| 8 | H | $NMe_2$ | H | H | O | 96 | 83 | 38 | 25 | NS | NS | NS | 185–186 | C |
| 9 | H | H | H | H | S | 17 | — | — | N.D. | N.D. | N.D. | N.D. | 253–255 | D |
| 10 | H | H | H | H | O | 89 | 59 | 14 | 23.0 | 10 | 22 | 31 | 210–212 | D |
| 11 | H | H | Br | H | S | 10 | 9 | — | N.D. | N.D. | N.D. | N.D. | 235 (dec.) | D |
| 12 | H | H | Br | H | O | 89 | 70 | 23 | 24.0 | 0 | 0 | 0 | 228–230 | D |
| 13 | H | H | H | Br | S | 46 | 16 | — | N.D. | N.D. | N.D. | N.D. | 270 (dec.) | D |
| 14 | H | H | H | Br | O | 93 | 79 | 36 | 23.0 | 0 | 40 | 50 | 253–255 | D |
| 15 | H | Cl | H | H | S | 43 | 14 | — | N.D. | N.D. | N.D. | N.D. | 230 (dec.) | D |
| 16 | H | Cl | H | H | O | 85 | 79 | 36 | 25.0 | 44 | 81 | 82 | 223–225 | D |
| 17 | H | I | H | H | S | 58 | 24 | — | 26 | 0.0 | 0.0 | 34.0 | 242–244 (dec.) | D |
| 18 | H | I | H | H | O | 94 | 89 | 59 | 24 | 33 | 63.0 | 74.0 | 226–228 | D |

Inhibition of Aldose Reductase by Compounds of Formula (III)

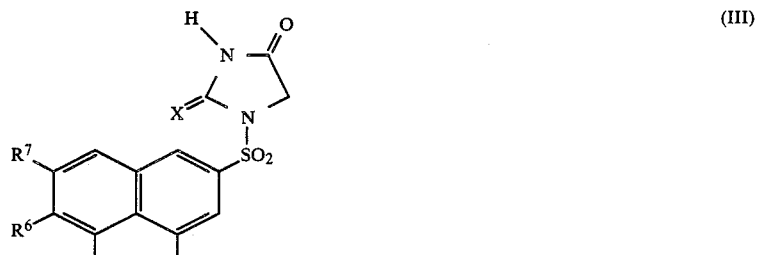

(III)

| 19 | H | Br | H | H | S | 13 | 9 | — | N.D. | N.D. | N.D. | N.D. | 250 (dec.) | A |
| 20 | H | Br | H | H | O | 89 | 77 | 24 | 24 | N.S. | N.S. | 70 | 292–294 | A |
| N—[[6-methoxy-5-(trifluoromethyl)-1-naphthalenyl]thioxomethyl]-N—methylglycine(tolrestat) | | | | | | — | — | 79 | 4 | 0 | 35 | 80 | — | — |
| | | | | | | | | | 11 | 14 | 86 | 89 | — | — |

(N.S. = nonsignificant
N.D. = not determined)

The Process

The naphthalenylsulfonylimidazolidinediones and their thioxo analogs were prepared by the following reaction schemes, wherein $R^4$, $R^5$, $R^6$ and $R^7$ are as defined above.

Process A
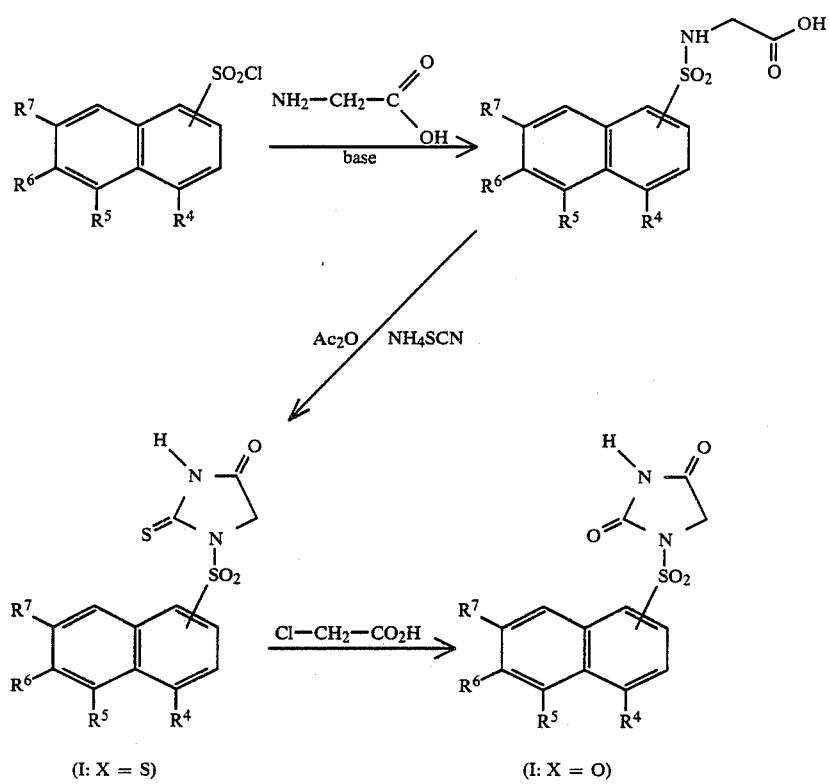
Process B
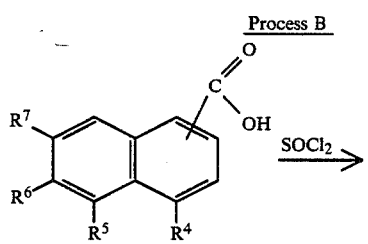
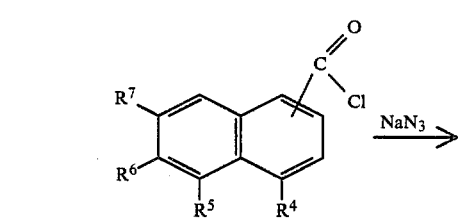
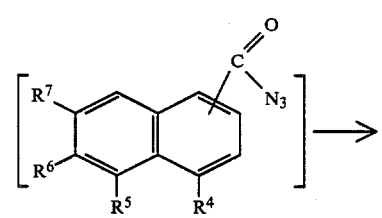
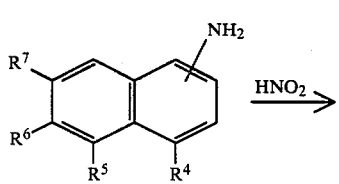
-continued
Process B
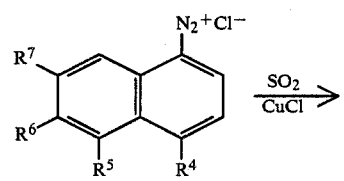
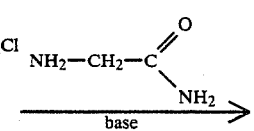
continued as in Process C
Process C Process D
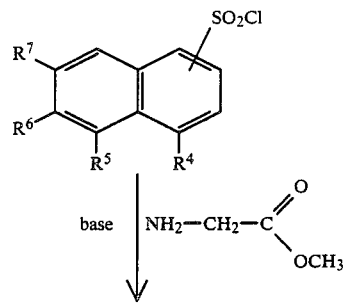
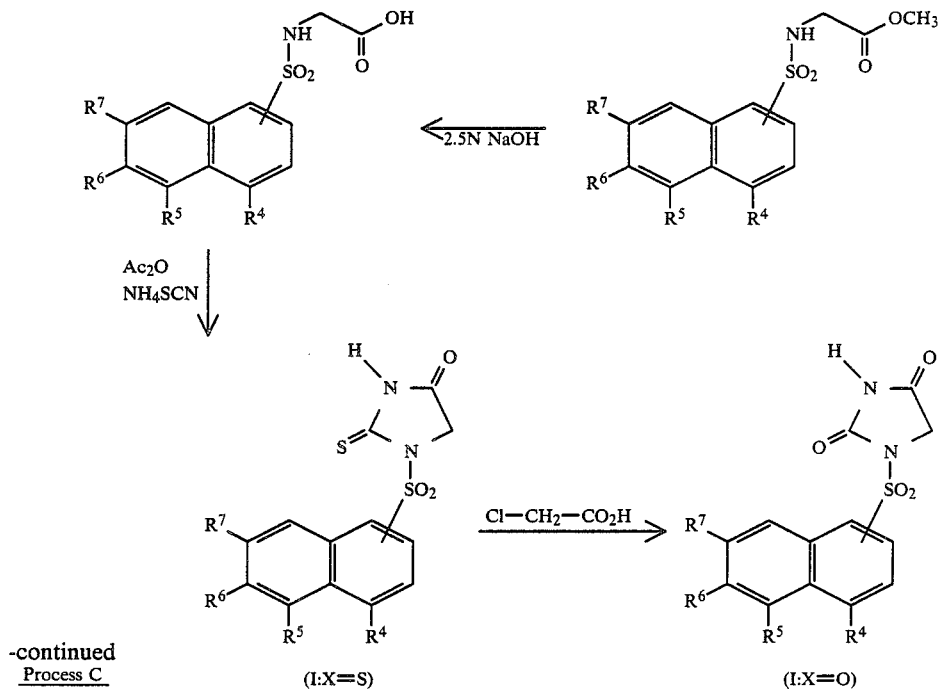
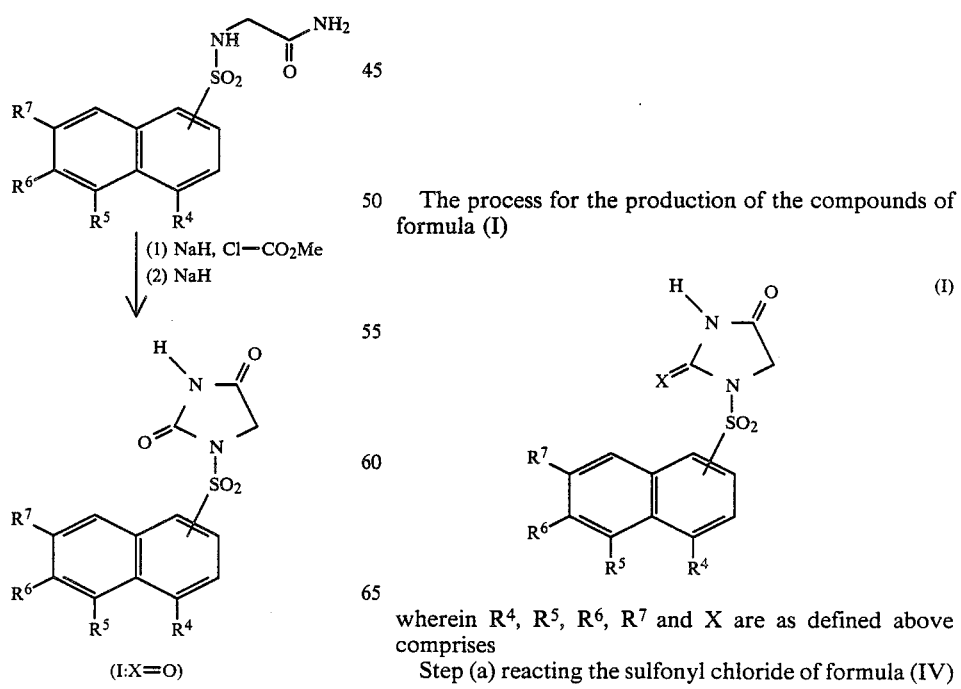
The process for the production of the compounds of formula (I)
(I)
wherein $R^4$, $R^5$, $R^6$, $R^7$ and X are as defined above comprises
Step (a) reacting the sulfonyl chloride of formula (IV)

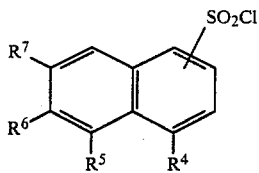

wherein $R^4$, $R^5$, $R^6$ and $R^7$ are as defined above with glycine (Process A), methyl glycinate (Process D) or glycinamide (Process B and C) to produce the sulfonyl glycine compound of formula (V)

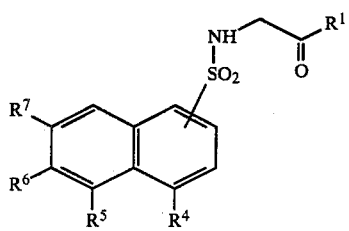

wherein $R^1$ is hydroxy, methoxy or amino respectively and $R^4$, $R^5$, $R^6$ and $R^7$ are as defined above.

Step (a) is carried out in the presence of base to neutralize the acid formed during the reaction.

The sulfonyl chlorides of formula (IV) required for the present invention are commercially available compounds or can be prepared by known methods. One such method is illustrated in Process B herein below wherein the corresponding carboxylic acid is converted to the required sulfonyl chloride via the azide and amine by conventional methods.

The sulfonyl chloride compound (IV) can be reacted with glycine directly (Process A). However, reaction with methyl glycinate (Process D) or with glycine having a suitable blocking group at the carboxylic end results in a higher yield and purer product. It is a preferred route even though the additional step (b) of hydrolyzing the esters of formula (V) wherein $R^1$ is methoxy to produce the compound of formula (V) wherein $R^1$ is hydroxy is required.

The compound of formula (V) wherein $R^1$ is hydroxyl is cyclized (step c) by reaction with ammonium thiocyanate, $NH_4SCN$ (Process A and D) in the presence of acetic anhydride to produce the thiohydantoin of formula (I:X=S)

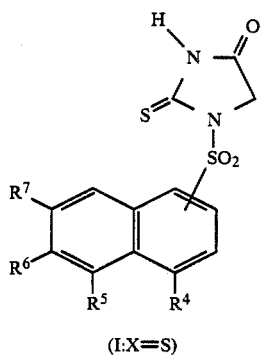

wherein $R^4$, $R^5$, $R^6$ and $R^7$ are as defined above. The compounds of structure (I:X=S) represents one group of compounds claimed in the present invention.

The thiohydantoins of formula (I:X=S) are hydrolyzed with chloroacetic acid, $ClCH_2CO_2H$ (step d) to produce the desired hydantoins of formula (I:X=O) (Process A and D)

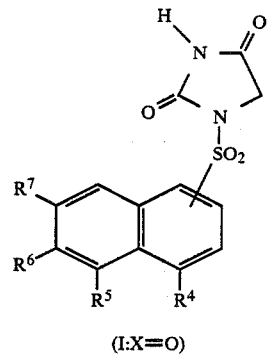

wherein $R^4$, $R^5$, $R^6$ and $R^7$ are as defined above. The compounds of structure (I:X=O) also represent a group of compounds claimed in the present invention.

The hydrolysis with chloroacetic acid requires drastic conditions such as heating at 100° C. to 140° C. for approximately 24 hours. In those cases where this process results in poor yields, the desired hydantoins (I:X=O) were obtained by (step e) cyclizing the compounds of formula (V) wherein $R^1$ is amino with sodium hydride and methyl chloroformate (Process B and C) to produce the desired hydantoins of formula (I:X=O) directly.

The chemical bases which are used as reagents in this invention to prepare the aforementioned pharmaceutically acceptable salts are those which form non-toxic salts with the various herein described acidic sulfonylmidazolidinediones and their thioxo analogs, such as 1-[(5-bromo-1-naphthalenyl)sulfonyl]-2,4-imidazolidinedione, for example. These particular non-toxic base salts are of such a nature that their cations are said to be essentially non-toxic in character over the wide range of dosage administered. Examples of such cations include those of sodium, potassium, calcium and magnesium, etc. These salts can easily be prepared by simply treating the aforementioned sulfonyl imidazolidinediones and their thioxo analogs with an aqueous solution of the desired pharmacologically acceptable cation and then isolating by filtration or evaporation the resulting salts.

Alternatively, they may also be prepared by mixing organic solutions of the said acidic compounds and the desired alkali metal hydroxide together and then isolating the resulting salts by precipitation in non-polar solvent. In either case, stoichiometric quantities of reagents must be employed in order to ensure completeness of reaction and maximum production yields with respect to the desired final product.

Compound 1-[[5-(dimethylamino)-1-naphthalenyl]-sulfonyl]-2,4-imidazolidinedione and its thioxo analog can also be used as the hydrochloride salt. This salt is a result of the basic 5-dimethylamino group. Passage of gaseous hydrochloric acid through an ethereal solution of the said compound gives the hydrochloride salt.

The following Examples further illustrate this invention.

PROCESS A

Example 1

1-[(5-Bromo-1-naphthalenyl)sulfonyl]-2-thioxo-4-imidazolidinone (II:$R^4$, $R^6$, $R^7$=—H, $R^5$=—Br, X=S)

Step (a) Preparation of [(5-Bromo-1-naphthalenyl)sulfonyl]glycine.

To a mixture of [(5-bromo-1-naphthalenyl)sulfonyl]chloride (5 g, 16.36 mmol), glycine (1.23 g, 16.36 mmol) in dioxane (25 mL) was added dropwise aqueous saturated $Na_2CO_3$ until pH~7.5-8. After stirring for 30 minutes, the mixture was acidified by HCl (1N) and the precipitated solid filtered, washed with $H_2O$ and dried. The crude product was recrystallized from hot $H_2O$ to yield a white solid m.p. 215°-216° C. (4.2 g, 74.6%).

IR (KBr, cm$^{-1}$) 3340 (s), 1715 (s), 1410 (m), 1310 (s), 1120 (s), 780 (s).

NMR (DMSO-$d_6$, 200 MHz) δ 3.67 (d, J=6 Hz, 2H), 7.63 (dd, J=8.4 Hz, 1H), 7.79 (dd, J=7.9 Hz, 1H), 8.06 (d, J=7.8 Hz, 1H), 8.22 (d, J=8.0 Hz, 1H), 8.46 (d, J=8.6 Hz, 1H), 8.55 (t, J=6.0 Hz, 1H), 8.73 (d, J=8.4 Hz, 1H).

UV (MeOH): $\lambda_{max}$ 222.0 nm (ε 32700), 297.5 nm (ε 8110).

M/S: m/e 343 (M—H)$^+$, 269 (M$^+$-NHCH$_2$CO$_2$H), 126 (M$^+$, —Br, -[(sulfonyl)-2-thioxo-4-imidazolidinone].

Anal. Calcd: C, 41.86; H, 2.90; N, 4.07. Found: C, 41.64; H, 3.15; N, 4.17.

Step (b) Preparation of 1-[(5-Bromo-1-naphthalenyl)sulfonyl]-2-thioxo-4-imidazolidinone According to the process of J. Okuda et al, Chem. Pharm. Bull. 30(9), 3244-3254 (1982), a mixture of [(5-bromo-1-naphthalenyl)sulfonyl]glycine (9.25 g, 26.89 mmol), acetic anhydride (6.34 mL, 67.21 mmol) and NH$_4$SCN (2.66 g, 34.95 mmol) in dry pyridine (30 mL) was heated to 110° C. for 1 hour. Then the pyridine was removed in vacuo, $H_2O$ (150 mL) was added and the mixture was stirred for 1 hour. The brown solid was filtered, washed with $H_2O$, dried and recrystallized (twice) from DMF/$H_2O$ to yield a white solid m.p. 235°-237° C. (6.9 g, 66.7%).

IR (KBr, cm$^{-1}$) 3210 (m), 1750 (s), 1355 (s), 1170 (s), 780 (s).

NMR (DMSO-$d_6$, 200 MHz) δ 5.02 (s, 2H), 7.7 (dd, J=7.8 Hz, 1H), 7.91 (dd, J=7.8 Hz, 1H), 8.13 (d, J=7.2 Hz, 1H), 8.45 (d, J=8.6 Hz, 1H), 8.62 (d, J=7.8 Hz, 2H).

UV (MeOH): $\lambda_{max}$ 212.5 nm (ε 26900), 234.5 nm (ε 29600), 267.5 nm (ε 11800), 309.5 nm (ε 6310).

M/S: m/e 385 (M+H)$^+$, 271 (M$^+$-2-thioxo-4-imidazolidinone), 117 (M$^+$, -Br, -[(sulfonyl)-2-thioxo-4-imidazolidinone)].

Anal. Calcd: C, 40.62; H, 2.34; N, 7.29. Found: C, 40.56; H, 2.66; N, 7.18.

Example 2

1-[(5-Bromo-1-naphthalenyl)sulfonyl]-2,4-imidazolidinedione (II:$R^4$, $R^6$, $R^7$=—H, $R^5$=—Br, X=O)

According to the procedure of H. C. Brimelow et al, J. Chem. Soc., 2789-2796 (1962) a mixture of 1-[(5-bromo-1-naphthalenyl)sulfonyl]-2-thioxo-4-imidazolidinone (prepared in Example 1) (1.7 g, 4.41 mmol), ClCH$_2$CO$_2$H (10 g, 105.8 mmol) and $H_2O$ (0.3 mL) was heated to 120° C. for 24 hours. The mixture was diluted with $H_2O$ (100 mL) and cooled to 0° C. for 1 hour. The precipitated solid was filtered, washed with $H_2O$ and recrystallized from acetone/$H_2O$ to yield a white solid m.p. 227°-228° C. (1.52 g, 85.9%).

IR (KBr, cm$^{-1}$) 3170 (m), 1800 (s), 1750 (s), 1370 (s), 1170 (s), 785 (s).

NMR (DMSO-$d_6$, 200 MHz) δ 4.66 (s, 2H), 7.69 (dd, J=7.6 Hz, 1H), 7.91 (dd, J=7.6 Hz, 1H), 8.12 (d, J=7.4 Hz, 1H), 8.54 (d, J=8.0 Hz, 1H), 8.63 (m, 2H), 11.67 (s, 1H).

UV (MeOH): $\lambda_{max}$213.5 nm (ε29700), 236.5 nm (ε25200), 303.5 nm (ε7560).

M/S: m/e 369 (M+H)$^+$.

Anal. Calcd: C, 42.27; H, 2.44; N, 7.58. Found: C, 42.19; H, 2.71; N, 7.56.

PROCESS B

Example 5

1-[[6-Methoxy-5-(trifluoromethyl)-1-naphthalenyl]sulfonyl]-2,4-imidazolidinedione (II:X=O, $R^4$, $R^7$=—H, $R^5$=—CF$_3$, $R^6$=—OCH$_3$)

Step (a) Preparation of 6-Methoxy-5-(trifluoromethyl)-1-naphthalene amine.

6-Methoxy-5-(trifluoromethyl)-1-naphthalenecarboxylic acid (30.0 g, 1.11×10$^{-1}$M) was stirred in thionyl chloride (120 mL) at 20° C. under nitrogen. Dimethylformamide (0.75 mL, anhydrous) was added, and the mixture was refluxed for 4 hours. The solvent and excess of thionyl chloride were evaporated under reduced pressure. Toluene (200 mL) was added, the solvent re-evaporated and the residual solid was dried (20° C./0.1 mm). The white solid was dissolved in acetone (300 mL), cooled to 0° C. and a solution of sodium azide (7.8 g, 1.19×10$^{-1}$M) in water (25 mL) was added dropwise (precipitate formation). The mixture was stirred at 0° C. for 30 minutes, diluted to 600 mL volume with water, stirred for 1 hour at 0° C., filtered, and the filtered solid was washed with water (2×200 mL). The damp solid (Any azides are generally unsafe to handle.) was dissolved in toluene (400 mL), and the filtrate concentrated to 280 mL under reduced pressure, refluxed for 1 hour, then cooled to 20° C. Potassium hydroxide (40% aq, 200 mL) was added. The resultant mixture was refluxed for 1 hour, cooled to 30° C., and filtered. The filtered solid (This solid is an unwanted side product. Care should be taken to avoid precipitation of the desired product from toluene during filtration.) was washed with water (200 mL), and toluene (200 mL). The filtrate and washings were combined. The organic layer was separated, washed with water (200 mL), dried (MgSO$_4$), filtered, and solvent evaporated to furnish the product (19.0 g, 84%) m.p. 120° C. as a white powder.

NMR (DMSO-$d_6$, 200 MHz) δ 4.05 (s, 3H, —OCH$_3$), 5.80 (s, 2H, —NH$_2$), 6.75-8.50 (m, 5H, ArH).

M/S: (m/e) 241 (M$^+$).

Step (b) Preparation of 6-Methoxy-5-(trifluoromethyl)-1-naphthalenesulfonyl Chloride 6-Methoxy-5-(trifluoromethyl)-1-naphthalene amine (2.7 g 1.12×10$^{-2}$M) was added in one portion to a mixture of concentrated hydrochloric acid (10 ML) and glacial acetic acid (5 mL) with mechanical stirring. The white hydrochloride salt precipitated. The flask was placed over a dry ice-ethanol bath, and shaken. When the temperature of the stirred mixture reached −10° C., a solution of sodium nitrite (1.0 g, 1.45×10$^{-2}$M) in water (5 mL) was added dropwise at such a rate that the temperature did not exceed −5° C. After all the sodium nitrite solution was added, the mixture was stirred for 1 hour while the temperature was maintained between −10° C., and −5° C. While the diazotization was being completed, glacial acetic acid (30 mL) was saturated with sulfur dioxide (gas), cuprous chloride (0.44 g, $4.44 \times 10^{-3}$M) was added, and the introduction of sulfur dioxide was continued until the yellow-green suspension became blue-green. The mixture was cooled to 20° C., and the diazotization reaction mixture was added, warmed slowly to 50° C., stirred at 50° C. (1 hour), until foaming ceased, then cooled, and poured into ice water (300 mL). The resultant mixture was extracted with ether (2×100 mL). The combined organic layer was washed with water (3×100 mL), saturated aqueous sodium bicarbonate until neutral, then with water (100 mL), dried (MgSO$_4$) filtered and evaporated under reduced pressure to yield an oil, which was flash chromatographed on silica gel (6% ethyl acetate-hexane) to yield the product as a yellow solid. The yellow solid was recrystallized from ether hexanes to yield the pure product (1.8 g, 50%) m.p. 60°–62° C. as a white crystalline solid.

NMR (CDCl$_3$, 200 MHz) δ 4.08 (s, 3H, —OCH$_3$), 7.60–9.10 (m, 5H, ArH).

M/S: (m/e) 324 (M+), 177.

IR (CHCl$_3$, cm$^{-1}$) 1610, 1590 (—C=C).

Anal. Calcd: C, 44.39; H, 2.48. Found: C, 44.28; H, 2.80.

Step (c) Preparation of [[[6-Methoxy-5-(trifluoromethyl)-1-naphthalenyl]-sulfonyl]amino]acetamide.

A saturated aqueous sodium carbonate solution (3 mL) was added to a solution of 6-methoxy-5-(trifluoromethyl)-1-naphthalenesulfonyl chloride (5.5 g, 16.9 mmol) and glycine amide (2.50 g, 33.7 mmol) in dioxane (30 mL) at 20° C., until the reaction pH remained constant at ca. 8.5. The reaction mixture was stirred for 16 hours at 20° C., then concentrated by rotary evaporation. Water (50 mL) was added, and the precipitated white solid was filtered and dried at 60° C./0.1 mm to give (5.98 g, 97.8%) m.p. 213°–215° C. of product.

NMR (DMSO-d$_6$, 200 MHz) δ 3.55 (s, 2H, NCH$_2$), 4.05 (s, 3H, —OCH$_3$), 7.0 (br s, 1H, CONH), 7.20 (br s, 1H, CONH)

M/S: (m/e) 363 (M)+, 225.

IR (KBr, cm$^{-1}$) 3450, 3320 (CONH$_2$), 1675 (C=O), 1615, 1600 (C=C).

Step (d) Preparation of 1-[[6-Methoxy-5-(trifluoromethyl)-1-naphthalenyl]-sulfonyl]-2,4-imidazolidinedione.

Sodium hydride (0.40 g, 16.6 mmol) was added to a solution of [[[6-methoxy-5-trifluoromethyl)-1-naphthalenyl]sulfonyl]amino]acetamide (5.5 g, 15.1 mmol) in dimethylformamide (anhydrous, 50 mL), at 20° C., under a nitrogen atmosphere and stirred for 30 minutes. Methyl chloroformate (1.16 mL, 15.1 mmol) was added, with the resultant reaction temperature rising to 50° C. The reaction was stirred at 20° C. for 3 hours, then the volatile solvents were evaporated by rotary evaporation. Sodium hydride (0.40 g, 16.6 mmol) was added, and the mixture was heated at 75° C. for 2 hours, and cooled to 20° C. Water (30 mL) was added and the precipitated solid was filtered, washed with water (30 mL) and recrystallized from methanol-water to furnish the pure product (2.0 g, 34%) m.p. 273° C. as a white crystalline solid.

NMR (DMSO-d$_6$, 200 MHz) δ 4.04 (s, 3H, —OCH$_3$), 4.60 (s, 2H, NCH$_2$), 7.8–7.9 (m, 2H, ArH), 8.32 (d, 1H, ArH), 8.43 (d, 1H, ArH), 8.87 (d, 1H, ArH), 12.35 (s, 1H).

M/S: (m/e) 389 (M+H)+.

IR (KBr, cm$^{-1}$) 3400, 3200 (NH), 1800, 1765 (C=O), 1615, 1600 (C=C).

UV (MeOH): λ$_{max}$235.0, 289, 300, 339.5.

Anal. Calcd: C, 46.09; H, 2.85; N, 7.21. Found: C, 45.89; H, 2.97; N, 7.20.

PROCESS C

Example 7

1-[[5-(Dimethylamino)-1-naphthalenyl]sulfonyl]-2,4-imidazolidinedione (II: X=O, R$^4$, R$^6$, R$^7$=—H, R$^5$=—N(CH$_3$)$_2$)

Step (a) Preparation of [[5-(Dimethylamino)-1-naphthalenyl]sulfonyl]glycinamide

To a mixture of [[5-(dimethylamino)-1-naphthalenyl]-sulfonyl]chloride (dansyl chloride) (5.0 g, 18.53 mmol) glycinamide hydrochloride (2.05 g, 18.53 mmol) in dioxane (50 mL) was added dropwise aqueous saturated Na$_2$CO$_3$ until pH ~7.5–8. After stirring for 30 minutes the volatiles were removed in vacuo and H$_2$O (200 mL) added to the solid mass. The mixture was stirred for 5 minutes and the solid filtered and recrystallized from acetone/H$_2$O to yield a white solid (4.95 g, 86.9%), m.p. 116°–117° C.

IR (KBr, cm$^{-1}$) 3420 (s), 3320 (m), 3190 (m), 1705 (s), 1410 (m), 1150 (s).

NMR (DMSO-d$_6$, 200 MHz) δ 3.42 (d, J=6.0 Hz, 2H), 7.08 (br s, 1H), 7.19 (br s, 1H), 7.26 (d, J=7.6 Hz, 1H), 7.60 (m, 2H), 8.15 (m, 2H), 8.30 (d, J=8.6 Hz, 1H), 8.44 (d, J=8.4 Hz, 1H).

UV (MeOH): λ$_{max}$217.5 nm (ε33600), 150.5 nm (ε13600), 337.0 nm (ε4290).

M/S: m/e 308 (M+H)+, 234 (M+—NHCH$_2$CONH$_2$), 171 [(M+H)+—SO$_2$NHCH$_2$CONH$_2$].

Anal. Calcd: C, 54.72; H, 5.54; N, 13.68. Found: C, 54.75; H, 5.47; N, 13.60.

Step (b) Preparation of 1-[[5-(Dimethylamino)-1-naphthalenyl]sulfonyl]-2,4-imidazolidinedione.

To a solution of [[5-(dimethylamino)-1-naphthalenyl]-sulfonyl]glycinamide (4.4 g, 14.33 mmol) in DMF (80 mL) was added portionwise NaH (50% dispersion in oil, 687.8 mg, 14.33 mmol). After stirring for 2 hours, methyl chloroformate (1.21 mL, 15.67 mmol) was added dropwise and the mixture stirred for 20 minutes. The excess volatile methylchloroformate was removed in vacuo and the remaining mixture warmed to 70° C. and NaH/50% dispersion in oil, (87.8 mg, 14.33 mmol) was added portionwise and the mixture was stirred for 1 hour. The volatiles were removed in vacuo, and ice water was added carefully to the residue. Extraction with EtOAc and concentration in vacuo gave a yellow heavy oil, which was purified by flash chromatography (CHCl$_3$/MeOH 10/1) and recrystallized from MeOH (at −78° C.) to give a fine yellow powder (2.51 g, 52.6%) m.p. 185°–186° C.

IR (KBr, cm$^{-1}$) 3220 (m), 1800 (m), 1735 (s), 1360 (m), 1170 (s), 785 (m).

NMR (DMSO-d$_6$, 200 MHz) δ 2.84 (s, 6H), 4.64 (s, 2H), 7.32 (d, J=7.4 Hz, 1H), 7.67 (d, J=8.4 Hz, 1H), 7.75 (d, J=8.6 Hz, 1H), 8.16 (d, J=8.6 Hz, 1H), 8.38 (dd, J=7.8 Hz, 1H), 8.60 (d, J=8.6 Hz, 1H), 11.62 (s, 1H).

UV(MeOH): λ$_{max}$214.5 nm (ε38428), 254.0 nm (ε14400), 348.0 nm (ε4120).

M/S: m/e 333 (M)+, 171 (M+-[(sulfonyl)-2,4-imidozolidinedione].

Anal. Calcd: C, 54.05; H, 4.51; N, 12.61. Found: C, 53.77; H, 4.66; N, 12.53.

PROCESS D

Example 9

1-[(1-Naphthalenyl)sulfonyl]-2-thioxo-4-imidazolidinone (II: X=S, $R^4$, $R^5$, $R^6$, $R^7$=—H)

Step (a) Preparation of [(1-Naphthalenyl)sulfonyl]glycine Methyl Ester.

To a mixture of 1-naphthalenyl sulfonyl chloride (10.0 g, 44.15 mmol) in dioxane (200 mL) and methyl glycinate hydrochloride (5.54 g, 44.15 mmol) was added aqueous saturated $Na_2CO_3$ to pH=7.5. The mixture was stirred for 30 minutes and then was poured into $H_2O$ (500 mL), extracted with EtOAc, dried over $MgSO_4$ and concentrated. The product, white solid m.p. 68°–70° C. (11.9 g, 96.7%) was used in the next step without any further purification.

IR (KBr, $cm^{-1}$) 3300 (s), 1745 (s), 1440 (s), 1330 (s), 1160 (s), 1130 (s), 770 (s).

M/S: m/e 279M+, 220 (M+—$CH_3O$, —CO), 191 (M+—$NHCH_2CO_2Me$), 127 ($M^{30}$ —$SO_2$—$NHCH_2CO_2Me$).

NMR (DMSO-$d_6$, 200 MHz) δ 3.36 (s, 3H, —OMe), 3.75 (d, J=6.6 Hz, 2H, —$NHCO_2Me$), 7.67 (m, 3H, ArH̲), 8.11 (m, 3H, ArH̲), 8.64 (m, 2H, ArH̲, —$SO_2NHCH_2$—)

Step (b) Preparation of [(1-Naphthalenyl)sulfonyl]glycine.

To a mixture of (1-naphthalenyl)sulfonyl methyl glycinate (11.9 g, 42.65 mmol) in MeOH (200 mL) and THF (100 mL) was added NaOH (2.5N, 30 mL) and the mixture was stirred for 2 hours. The mixture was neutralized with HCl (2N) and the MeOH-THF were removed in vacuo. The residue was acidified with HCl (1N) and the mixture was extracted with EtOAc. The organic layer was dried over $MgSO_4$ and concentrated to yield a white solid (10.1 g, 89%) m.p. 133°–135° C.

IR (KBr, $cm^{-1}$) 3360 (s), 1720 (s), 1420 (s), 1310 (s), 1130 (s).

M/S: m/e 265 (M+), 220 (M+—CO, —OH), 191 (M+—$NHCH_2CO_2H$), 127 (M+—$SO_2NHCH_2CO_2H$).

NMR (DMSO-$d_6$, 200 MHz) δ 3.63 (d, J=6.0 Hz, 2H, —$NHCH_2CO_2H$), 7.66 (m, 3H, ArH̲), 8.15 (m, 3H, ArH̲), 8.43 (t, J=6.8 Hz, 1H, —$SO_2NHCH_2$—), 8.65 (d, J=8.2 Hz, 1H, ArH̲).

Step (c) Preparation of 1-[(1-Naphthalenyl)sulfonyl]-2-thioxo-4-imidazolidinone.

To a mixture of [(1-naphthalenyl)sulfonyl]glycine (8.0 g, 30.18 mmol) in anhydrous pyridine (100 mL) were added acetic anhydride (11.4 mL, 120.7 mmol), $NH_4SCN$ (2.87 g, 37.7 mmol) and the mixture was stirred at 100° C. for 1 hour. The pyridine was removed in vacuo and the residue was taken in EtOAc and washed with $H_2O$ and brine. The organic layer was dried over $MgSO_4$, concentrated, and the crude product was purified by recrystallization from acetone/$H_2O$ (at 0° C.) to yield a white solid (7.7 g, 83.4%) m.p. 253° C. (dec.).

IR (KBr, $cm^{-1}$) 3280 (s), 1790 (s), 1760 (s), 1455 (s), 1340 (s), 1160 (s), 1080 (s), 760 (s).

M/S: m/e 242 (M+—$SO_2$), 127 (M+-sulfonyl-2-thioxo-4-imidazolidinone).

UV (MeOH): $\lambda_{max}$271.0 nm (ε14900), 318.5 nm (ε4040).

NMR (DMSO-$d_6$, 400 MHz) δ 5.0 (s, 2H, —$NCH_2CO$—), 7.75 (m, 3H, ArH̲), 8.14 (d, J=7.8 Hz, 1H̲, ArH̲), 8.36 (m, 2H, ArH̲), 8.51 (d, J=7.6 Hz, 1H, ArH̲).

Anal. Calcd: C, 50.97; H, 3.29; N, 9.14. Found: C, 51.30; H, 3.39; N, 9.31.

Example 10

Preparation of 1-[(1-Naphthalenyl)sulfonyl]-2,4-imidazolidinedione (II: X=O, $R^4$, $R^5$, $R^6$, $R^7$=—H)

A mixture of 1-[(1-naphthalenyl)sulfonyl]-2-thioxo-4-imidazolidinone (3.0 g, 9.8 mmol) (prepared in Example 9), $ClCH_2CO_2H$ (20 g) and $H_2O$ (2 mL) was stirred at 135° C. for 24 hours. The mixture was poured into $H_2O$ and cooled to 0° C. The precipitated white solid was filtered and recrystallized from acetone/$H_2O$ (at 0° C.) to yield a white solid (1.8 g, 63.4%) m.p. 210°–212° C.

IR (KBr, $cm^{-1}$) 3460 (w), 3070 (s), 1790 (s), 1735 (s), 1350 (s), 1150 (s), 760 (s).

UV (MeOH): $\lambda_{max}$293.5 nm (ε6930), 318.5 nm (ε2900).

M/S: m/e 290 (M+), 226 (M+—$SO_2$), 127 (M+-sulfonyl-2,4-imidazolidinedione)

NMR (DMSO-$d_6$, 400 MHz)δ 4.68 (s, 2H, —$NCH_2CO$—), 7.80 (m, 3H, ArH̲), 8.18 (d, J=7.6 Hz, 1H̲, ArH̲), 8.40 (m, 2H, ArH̲), 8.58 (d, J=8.2 Hz, 1H, ArH̲), 11.65 (s, 1H, —CO—NH̲—CO).

Anal. Calcd: C, 53.79; H, 3.47; N, 9.65. Found: C, 53.45; H, 3.29; N, 9.90.

PROCESS A

Example 19

1-[(5-Bromo-2-naphthalenyl)sulfonyl]-2-thioxo-4-imidazolidinone (III: X=S, $R^4$, $R^6$, $R^7$=—H, $R^5$=—Br)

Step (a) Preparation of [(5-Bromo-2-naphthalenyl)sulfonyl]-N-glycine Methyl Ester.

To a mixture of 2-naphthalenyl sulfonyl chloride (13.0 g, 42.55 mmol), methyl glycinate hydrochloride (5.43 g, 42.55 mmol) and dioxane (200 mL) was added dropwise saturated $Na_2CO_3$ to pH=7.5. After stirring for 30 minutes the mixture was poured into $H_2O$ and extracted with EtOAc. The product (13.5 g) in the form of a white solid was used in the next step without further purification.

NMR (200 MHz, DMSO-$d_6$) δ 3.58 (s, 3H, —$CO_2CH_3$), 3.83 (d, J=5.6 Hz, 2H, —$NHCH_2CO_2Me$), 7.6 (dd, J=7.6 Hz, 1H, Ar-H̲), 8.03 (m, 2H̲, Ar-H̲), 8.3 (m, 2H, Ar-H̲), 8.5 (m, 2H, Ar-H̲, —$SO_2NHCH_2CO_2Me$).

Step (b) Preparation of [(5-Bromo-2-naphthalenyl)sulfonyl]-N-glycine.

A mixture of [(5-bromo-2-naphthalenyl)sulfonyl]-N-glycine methyl ester (13.0 g, 36.31 mmol) MeOH (150 mL), THF (100 mL) and NaOH (2.5N, 20 mL) was stirred for 1 hour. Next the mixture was acidified to pH ~4–5 and the volatiles were removed in vacuo. The residue was recrystallized from acetone/$H_2O$ to yield product m.p. 191°–193° C. in the form of a yellow solid (10.6 g, 84.9%).

NMR (400 MHz, DMSO-$d_6$) δ 3.66 (d, J=5.6 Hz, 2H, —$NHCH_2CO_2Me$), 7.6 (dd, J=7.6 Hz, 1H, Ar-H̲), 8.0 (m, 2H, Ar-H̲), 8.25 (m, 3H, Ar-H̲, —$SO_2NHCH_2$—), 8.5 (d, J=2.0 Hz, 1H, Ar-H̲).

IR (KBr, $cm^{-1}$) 3280 (s), 1735 (s), 1260 (s), 1165 (s).

Anal. Calcd.: C 41.88; H 2.93; N 4.07. Found: C 41.69; H 2.92; N 4.11.

Step (c) Preparation of 1-[(5-Bromo-2-naphthalenyl)-sulfonyl]-2-thioxo-4-imidazolidinone.

To a mixture of [(5-bromo-2-naphthalenyl)sulfonyl]-N-glycine (10.7 g, 31.10 mmol) in anhydrous pyridine (100 mL) were added acetic anhydride (11.74 mL, 124.4 mmol), and NH₄SCN (2.96 g, 38.87 mmol). The mixture was stirred at 100° C. for 1 hour and the pyridine was removed in vacuo. The residue was taken in H₂O and the mixture stirred for 1 hour. Next the precipitated solid was filtered and was recrystallized from DMF/H₂O (at 0° C.) to yield a white solid (9.0 g, 75.5%) m.p. 250 (dec.).

NMR (DMSO-d₆, 400 MHz) δ 4.88 (s, 2H, —NCH₂CO—), 7.65 (dd, J=8.6 Hz, 1H, Ar-H), 8.14 (d, J=7.0 Hz, 1H, Ar-H), 8.27 (m, 3H, Ar-H), 8.89 (d, J=1.6 Hz, 1H, Ar-H)

IR (KBr, cm⁻¹) 1755 (s), 1170 (s), 1080 (s).

Anal. Calcd.: C, 40,53; H, 2.35; N, 7.97. Found: C, 40.36; H, 2.39; N, 7.39.

Example 20

1-[(5-Bromo-2-naphthalenyl)sulfonyl]-2,4-imidazolidinedione (III: X=O, R⁴, R⁶ R⁷=—H, R⁵=—Br)

A mixture of 1-[(5-bromo-2-naphthalenyl)sulfonyl]-2-thioxo-4-imidazolidinone (2.5 g), ClCH₂CO₂H (15 g) and H₂O (1.0 mL) was stirred at 130° C. for 15 hours. Next, the mixture was poured into H₂O and cooled to 0° C. The precipitated solid was filtered and recrystallized from acetone/H₂O (at 0° C.) to yield a white solid (1.92 g, 80.3%), m.p. 292°–294° C.

NMR (DMSO-d₆, 400 MHz) δ 4.58 (s, 2H, —NCH₂CO—), 7.65 (dd, J=8.0 Hz, 1H, Ar-H), 8.2 (dd, J=9.0 Hz, 2H, Ar-H), 8.34 (dd, 8.6 Hz, 2H, Ar-H), 8.8 (s, 1H, Ar-H), 11.64 (s, 1H, —C0NHCO—).

IR (KBr, cm⁻¹) 3220 (s), 1740 (s), 1370 (s), 1160 (s).

Anal. Calcd.: C 42.29; H 4.26; N 7.59. Found: C 42.21; H 2.49; N 7.70.

Example 21

Preparation of 1-[(5-Bromo-1-naphthalenyl)sulfonyl]-2,4-imidazolidinedione Sodium Salt (II: R⁴, R⁶, R⁷=—H, R⁵=—Br, X=O; sodium salt)

To a solution of NaOH (98.1%, 5.52 mg) in H₂O (1.0 mL) was added 1-[(5-bromo-1-naphthalenyl)sulfonyl]-2,4-imidazolidinedione (50 mg, 0.135 mmol) and the suspension was stirred for 2 hours. The volatiles were removed in vacuo and the residue was taken up in a small amount of H₂O (0.5 mL) and acetone (1.0 mL). The precipitated solid was filtered and dried to yield a pale yellow solid (36.7 mg), m.p. 290° C. (dec.).

IR (KBr, cm⁻¹) 1610 (s), 1370 (s), 1065 (s), 790 (s).

NMR (200 MHz, DMSO-d₆) δ 4.01 (s, 2H, NCH₂CO), 7.64 (t, J=8.6 Hz, 1H, Ar-H), 7.84 (t, J=7.8 Hz, 1H, Ar-H), 8.07 (t, J=8.0 Hz, 1H, Ar-H), 8.34 (d, J=7.6 Hz, 1H, Ar-H), 8.52 (d, J=8.6 Hz, 1H, Ar-H), 8.67 (d, J=8.4 Hz, 1H, Ar-H).

MA: (C₁₃H₈BrN₂O₄SNa.1.3H₂O).

Calcd.: C, 37.64; H, 2.56; N, 6.75. Found: C, 37.69; H, 2.48; N, 6.58.

Example 22

Preparation of 1-[(5-Bromo-1-naphthalenyl)sulfonyl]-2,4-imidazolidinedione, Calcium Salt (II: R⁴, R⁶, R⁷=—H, R⁵=—Br, X=O; calcium salt)

To a solution of Ca(OH)₂ (8.0 mg) in H₂O (1 mL) was added 1-[(5-bromo-1-naphthalenyl)sulfonyl]-2,4-imidazolidinedione (80 mg) and the mixture was stired for 2 hours. The precipitated solid was filtered, washed with H₂O, hexane and dried to yield a pale yellow solid (55 mg), m.p. 225° C. (dec.).

IR (KBr, cm⁻¹) 1600 (s), 1355 (s), 1080 (s), 790 (s).

NMR (200 MHz, DMSO-d₆) δ 4.05 (s, 2H, NCH₂CO), 7.7 (t, J=9.2 Hz, 1H, Ar-H), 7.85 (t, J=8.6 Hz, 1H, Ar-H), 8.04 (d, J=7.4 Hz, 1H, Ar-H), 8.37 (d, J=7.6 Hz, 1H, Ar-H), 8.53 (d, J=8.6 Hz, 1H, Ar-H), 8.68 (d, J=8.2 Hz, 1H, Ar-H)

MA: (C₂₆H₁₆Br₂N₄O₈S₂Ca.2.0H₂O).

Calcd.: C, 38.40; H, 2.46; N, 6.89. Found: C, 38.37; H, 2.19; N, 6.60.

Example 23

Preparation of 1-[(5-Bromo-1-naphthalenyl)sulfonyl]-2,4-imidazolidinedione, Sodium Salt (II: R⁴, R⁶, R⁷=—H, R⁵=—Br, X=O; sodium salt)

To a solution of 1-[(5-bromo-1-naphthalenyl)sulfonyl]-2,4-imidazolidinedione (100 mg) in THF (3 mL), DMF (0.5 mL) was added NaH (8.13 mg) and the mixture was stirred for 2 hours. The reaction mixture was filtered into a hexane solution and stirred for 30 minutes. The precipitated solid was filtered, washed with hexane and dried to yield a pale yellow solid (88 mg), m.p. 290° C. (dec.).

IR (KBr, cm⁻¹) 1610 (s), 1370 (s), 1065 (s), 790 (s).

NMR (200 MHz, DMSO-d₆) δ 4.01 (s, 2H, NCH₂CO), 7.64 (t, J=8.6 Hz, 1H, Ar-H), 7.84 (t, J=7.8 Hz, 1H, Ar-H), 8.07 (t, J=8.0 Hz, 1H, Ar-H), 8.34 (d, J=7.6 Hz, 1H, Ar-H), 8.52 (d, J=8.6 Hz, 1H, Ar-H), 8.67 (d, J=8.4 Hz, 1H, Ar-H).

MA: (C₁₃H₈BrN₂O₄SNa).

Calcd.: C, 39.91; H, 2.06; N, 7.16. Found: C, 39.75; H, 2.30; N, 7.40.

We claim:

1. A compound of the formula (I)

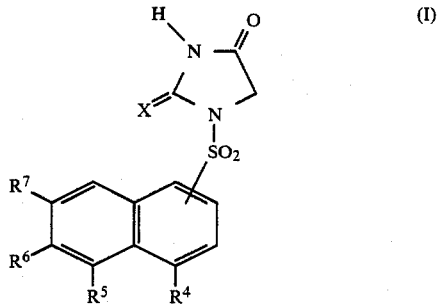

wherein R⁴, R⁵, R⁶ and R⁷ are hydrogen, halogen, trifluoromethyl, methoxy or dimethylamine and X is oxygen or sulfur and the pharmaceutically acceptable salts thereof.

2. A compound according to claim 1 of formula (II)

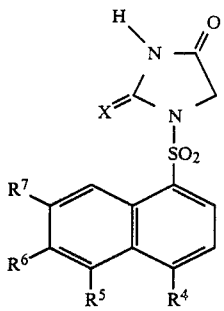

(II)

wherein $R^4$, $R^5$, $R^6$ and $R^7$ are hydrogen, halogen, trifluoromethyl, methoxy or dimethylamine and X is oxygen or sulfur and the pharmaceutically acceptable salts thereof.

3. The compound according to claim 2 wherein $R^4$, $R^5$, $R^6$ and $R^7$ are hydrogen or halogen and X is sulfur or oxygen, and the pharmaceutically acceptable salts thereof.

4. The compound according to claim 3 wherein $R^4$, $R^6$ and $R^7$ are hydrogen, $R^5$ is halogen and X is oxygen, and the pharmaceutically acceptable salts thereof.

5. The compound according to claim 4 designated 1-[(5-bromo-1-naphthalenyl)sulfonyl]-2,4-imidazolidinedione, and the pharmaceutically acceptable salts thereof.

6. The compound according to claim 3 designated 1-[(5-bromo-1-naphthalenyl)sulfonyl]-2-thioxo-4-imidazolidinone, and the pharmaceutically acceptable salts thereof.

7. The compound according to claim 4 designated 1-[(4-bromo-1-naphthalenyl)sulfonyl]-2,4-imidazolidinedione, and the pharmaceutically acceptable salts thereof.

8. The compound according to claim 3 designated 1-[(4-bromo--naphthalenyl)sulfonyl]-2-thioxo-4-imidazolidinone, and the pharmaceutically acceptable salts thereof.

9. The compound according to claim 2 designated 1-[[6-methoxy-5-(trifluoromethyl)-1-naphthalenyl]sulfonyl]-2,4-imidazolidinedione, and the pharmaceutically acceptable salts thereof.

10. The compound according to claim 2 designated 1-[[6-methoxy-5-(trifluoromethyl)-1-naphthalenyl]sulfonyl]-2-thioxo-4-imidazolidinone, and the pharmaceutically acceptable salts thereof.

11. The compound according to claim 2 designated 1-[[5-(dimethylamino)-1-naphthalenyl]sulfonyl]-2,4-imidazolidinedione and the pharmaceutically acceptable salts thereof.

12. The compound according to claim 2 designated 1-[[5-(dimethylamino)-1-naphthalenyl]sulfonyl]-2-thioxo-4-imidazolidinone and the pharmaceutically acceptable salts thereof.

13. The compound according to claim 3 designated 1-[(1-naphthalenyl)sulfonyl]-2-thioxo-4-imidazolidinone, and the pharmaceutically acceptable salts thereof.

14. The compound according to claim 4 designated 1-[(1-naphthalenyl)sulfonyl]-2,4-imidazolidinedione, and the pharmaceutically acceptable salts thereof.

15. The compound according to claim 3 designated 1-[(6-bromo-1-naphthalenyl)sulfonyl]-2-thioxo-4-imidazolidinone, and the pharmaceutically acceptable salts thereof.

16. The compound according to claim 4 designated 1-[(6-bromo-1-naphthalenyl)sulfonyl]-2,4-imidazolidinedione, and the pharmaceutically acceptable salts thereof.

17. The compound according to claim 3 designated 1-[(7-bromo-1-naphthalenyl)sulfonyl]-2-thioxo-4-imidazolidinone, and the pharmaceutically acceptable salts thereof.

18. The compound according to claim 4 designated 1-[(7-bromo-1-naphthalenyl)sulfonyl]-2,4-imidazolidinedione, and the pharmaceutically acceptable salts thereof.

19. The compound according to claim 3 designated 1-[(5-iodo-1-naphthalenyl)sulfonyl]-2-thioxo-4-imidazolidinone, and the pharmaceutically acceptable salts thereof.

20. The compound according to claim 4 designated 1-[(5-iodo-1-naphthalenyl)sulfonyl]-2,4-imidazolidinedione, and the pharmaceutically acceptable salts thereof.

21. The compound according to claim 4 designated 1-[(5-chloro-1-naphthalenyl)sulfonyl]-2,4-imidazolidinedione, and the pharmaceutically acceptable salts thereof.

22. The compound according to claim 3 designated 1-[(5-chloro-1-naphthalenyl)sulfonyl]-2-thioxo-4-imidazolidinone, and the pharmaceutically acceptable salts thereof.

23. The process for the production of the compounds of formula (I)

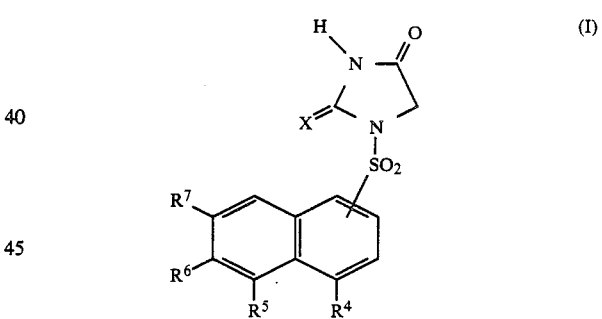

(I)

wherein $R^4$, $R^5$, $R^6$ and $R^7$ are hydrogen, halogen, trifluoromethyl, methoxy or dimethylamine and X is oxygen or sulfur which comprises, and the pharmaceutically acceptable salts thereof (a) reacting the compound of formula (IV)

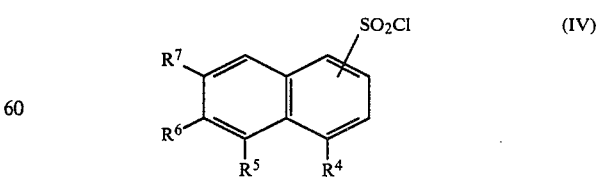

(IV)

wherein $R^4$, $R^5$, $R^6$ and $R^7$ are hydrogen, halogen, trifluoromethyl, methoxy or dimethylamine with glycine, methyl glycinate or glycinamide to produce the compound of formula (V)

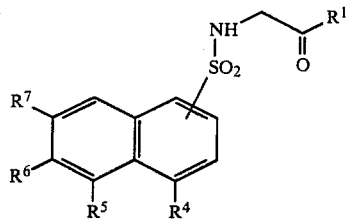

wherein $R^1$ is hydroxy, methoxy or amino respectively and $R^4$, $R^5$, $R^6$ and $R^7$ are as defined above (b) hydrolyzing the esters of formula (V) wherein $R^1$ is methoxy to produce the compound of formula (V) wherein $R^1$ is hydroxy (c) cyclizing the compound of formula (V) wherein $R^1$ is hydroxy with ammonium thiocyanate, $NH_4SCN$, in the presence of acetic anhydride to produce the thiohydantoin of formula (I:X=S)

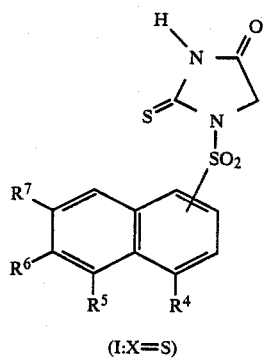

wherein $R^4$, $R^5$, $R^6$ and $R^7$ are as defined above (d) hydrolyzing the thiohydantoin of formula (I:X=S) with chloroacetic acid, $ClCH_2CO_2H$, to produce the hydantoins of formula (I:X=O)

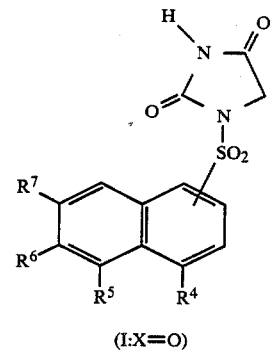

wherein $R^4$, $R^5$, $R^6$ and $R^7$ are as defined above (e) cyclizing the compounds of formula (V) wherein $R^1$ is amino with sodium hydride and methyl chloroformate to produce the hydantoins of formula (I:X=O) directly (f) treating the compounds of formula (I) with base to give the desired pharmaceutically acceptable salts.

24. A pharmaceutical composition for preventing or relieving neuropathy, nephropathy, retinopathy or cataracts in a diabetic mammal, which comprises an effective amount of a compound of claim 1 and a pharmaceutically acceptable carrier.

25. A method of preventing or relieving neuropathy, nephropathy, retinopathy or cataracts in a diabetic mammal, which comprises administering to said mammal an alleviating or prophylactic amount of a compound of claim 1.

* * * * *